United States Patent [19]

Janaky et al.

[11] Patent Number: 5,171,835

[45] Date of Patent: Dec. 15, 1992

[54] LHRH ANTAGONISTS

[75] Inventors: Tamas Janaky, Szeged; Atilla Juhasz, Budapest, both of Hungary; Andrew V. Schally, Metairie, La.

[73] Assignee: The Administrators of the Tulane Educational Fund, New Orleans, La.

[21] Appl. No.: 647,786

[22] Filed: Jan. 30, 1991

Related U.S. Application Data

[63] Continuation-in-part of Ser. No. 404,667, Sep. 7, 1989, abandoned, which is a continuation-in-part of Ser. No. 260,994, Oct. 21, 1988, abandoned.

[51] Int. Cl.$^5$ .............................................. C07K 7/20
[52] U.S. Cl. .................................. 530/313; 530/318; 514/900; 930/110; 930/130; 930/320
[58] Field of Search ............... 530/313, 318; 514/800, 514/15, 2; 930/110, 130, 320

[56] References Cited

U.S. PATENT DOCUMENTS

| | | | |
|---|---|---|---|
| 3,963,691 | 6/1976 | Hoffman et al. | 530/313 |
| 4,565,804 | 1/1986 | Rivier et al. | 514/15 |
| 4,800,191 | 1/1989 | Schally et al. | 530/313 |
| 4,851,385 | 7/1989 | Roeske | 530/313 |
| 4,935,491 | 6/1990 | Folkers et al. | 530/313 |

FOREIGN PATENT DOCUMENTS

| | | | |
|---|---|---|---|
| 0097031 | 12/1983 | European Pat. Off. | 530/313 |
| 2228262 | 8/1990 | United Kingdom | 530/313 |
| 9011298 | 10/1990 | World Int. Prop. O. | 530/313 |

OTHER PUBLICATIONS

Folkers et al, Biol. Chem. Sci., vol. 42, No. 1, pp. 101-106,(1987).
Hocart et al, J. Med. Chem., vol. 30, No. 10, pp. 1910-1914, (1987).
Nikolics et al., Peptides, vol. 5, pp. 1001-1006, (1984).
Ljungqvist et al, Biochemical and Biophysical Research Comm., vol. 148, No. 2, pp. 849-856, (1987).
Phillips et al, Life Sciences, vol. 43, pp. 883-888, (1988).
Nestor, Jr. et al, Journal of Med. Chem., vol. 25, No. 7, pp. 795-801, (1982).
Bajusz et al, Proc. Nat'l. Acad. Sci. U.S.A., vol. 86, pp. 6313-6317, (Aug. 1989).
Schröder et al, Peptides, vol. 1, pp. 23-27, (1965).

*Primary Examiner*—Merrell C. Cashion, Jr.
*Assistant Examiner*—T. D. Wessendorf
*Attorney, Agent, or Firm*—Omri M. Behr; Matthew J. McDonald

[57] ABSTRACT

Disclosed herein are analogues of the luteinizing hormone-releasing hormone (LH-RH), which are potent antagonists of LH-RH. These peptides inhibit the release of gonadotropins from the pituitary in mammals, including humans and possess antitumor activity.

Formula I represents peptides which are within the scope of this invention:

$$X—R^1—R^2—R^3—Ser—R^5—R^6(AY_2)—Leu—Arg—Pro—D—Ala—NH_2 \qquad I$$

and the pharmaceutically acceptable salts thereof, wherein $R^1$ is D-Phe, D-Phe(4Cl), D-Nal(1) or D-Nal(2),
$R^2$ is D-Phe or D-Phe(4HI),
$R^3$ is D-Trp, D-Phe, D-Phe(4HI), D-Nal(1), D-Nal(2) or D-Pal(3),
$R^5$ is Tyr or Arg,
$R^6$ is D-Lys or D-Orn,
HI is fluoro, chloro or bromo
X is a lower alkanoyl group of 2-5 carbon atoms,
A is a diaminoacyl residue having the formula $$\begin{array}{c} CH_2—(CH_2)_m—CH—(CH_2)_n—CO— \\ | \qquad\qquad\qquad | \\ NH_2 \qquad\qquad\qquad NH_2 \end{array} \qquad II$$

where
m is 0 or 1,
n is 0 or 1,
Y is $Y^1$ or $Y^2$, wherein
  $Y^1$ is an acyl group derived from straight or branched chain aliphatic, alicyclic carboxylic acids having from 3 to 12 carbon atoms or aromatic carboxylic acid of 6 or 10 ring carbon atoms,
  $Y^2$ is carbamoyl or alkyl-substituted carbamoyl group having the formula $$H—(CH_2)_n—NH—CO— \qquad III$$

where n is 0-3.

21 Claims, No Drawings

LHRH ANTAGONISTS

This invention was made with Government support under grant Nos. 40003 and 40004, awarded by the N.C.I. (NIH). The U.S. Government has certain rights in this application.

RELATED APPLICATIONS

This application is a continuation-in-part of copending application, Ser. No. 07/404,667 filed Sep. 7, 1989, which is a continuation-in-part of application Ser. No. 260,994 filed Oct. 21, 1988, now abandoned.

BACKGROUND OF THE INVENTION

The present invention is directed to novel peptides having an inhibitory effect on the release of gonadotropins by the pituitary in mammals, including humans and having an influence on the growth of cancerous tumors in humans. More specifically, the present invention relates to antagonistic analogs of luteinizing hormone-releasing hormone (LHRH), which have the structure:

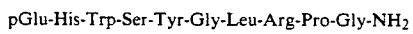

pGlu-His-Trp-Ser-Tyr-Gly-Leu-Arg-Pro-Gly-NH$_2$ salts thereof, and to pharmaceutical compositions and methods of use pertaining to these analogs.

DISCUSSION OF THE PRIOR ART

Hypothalamic luteinizing hormone-releasing hormone (LHRH) controls pituitary synthesis and secretion of gonadotropins (LH and FSH) that are essential for the regulation of the synthesis of sex steroids in the gonads.

Over 2500 new, synthetic analogs of LHRH (agonistic and antagonistic analogs) have been reported since its discovery and structural elucidation (A. V. Schally et al., Fertil. Steril. 22, 703-721, 1971) in view of their expected medical applications (M. J. Karten and J. E. Rivier, Endocrine Rev. 7, 44-66, 1986; A. Dutta, Drugs of the Future, 13 761-787, 1988). LHRH antagonists compete with endogeneous LHRH at the hypophysial receptors and directly inhibit the secretion of gonadotropins. They have significant therapeutic advantages over the agonists in that they almost immediately inhibit gonadotropin secretion without inducing an initial rise in gonadotropins, as is characteristic of LHRH agonists. Antagonists of LHRH have been used in endocrinology and gynecology to control fertility and treatment of precocious puberty, as they block ovulation in the female and suppress spermatogenesis in the male. The use of antagonists in oncology for treatment of hormone-sensitive tumors is very recent, but most promising (A. V. Schally et al., in: GnRH analogs in cancer and in human reproduction. Basic Aspects, (edited by B. H. Vickery and V. Lunenfeld), Kluwer Academic Publishers, Dordrecht/Boston/London, Vol. 1, pp. 5-31, 1989).

The most interesting antagonists to date have been compounds whose structure is a modification of the structure of LHRH. Systematic modification of the molecule showed the contribution of the individual amino acids and their side chains to the biological activity. The earlier most-potent antagonists frequently had a cluster of hydrophobic D-amino acid residues at the N-terminal and strongly basic, hydrophilic D-amino acids at position 6 and/or 8 (D. H. Coy et al., Endocrinology, 100 1445-1447, 1982; A. Horvath et al., Peptides 3 969-971, 1982; J. Rivier et al., J. Med. Chem. 29, 1846-1851, 1986). However, these potent, hydrophilic antagonists caused transient systemic edema of the face and extremities and inflamation at the injection site when injected subcutaneously into rats at 1.25 or 1.5 mg/kg body weight. These analogues, which are mast cell secretagogues, release histamine and, when given intravenously to rats at a dose of 1.25 mg/kg body weight, can also cause cyanosis and respiratory depression leading to cell death (Smith et al., Contraception 29, 283-289, 1984; Morgan et al., Int. Arch. Allergy Appl. Immunology 80, 70-75, 1986). To overcome these side effects but maintain the high antiovulatory potency of the antagonists, research was directed towards the change of the basicity of the side chains at the region of 5-8 amino acids. Hocart et al. (J. Med. Chem. 30, 1910-1914, 1987) found that the substitution of alkylated Lys derivatives in position 6 did not produced any significant changes in the histamine releasing activity of the analogues whereas similar substituents at position 8 reduced the histamine release 10-fold. Detirelix [Ac-D-Nal(2)$^1$,D-Phe(4Cl)$^2$,D-Trp$^3$,D-hArg-(Et)$_2$$^6$,D-Ala$^{10}$] proved to be a powerful antagonist (L. A. Adams et al., J. Clin. Endocrinol. Metab. 62, 58, 1986) but has hypotensive and bradycardic side effect (C. H. Lee et al., Life Sci., 45, 67, 1989). Antagonists named Nal-Glu-GnRHant retain ovulation inhibition potency and have markedly less in vitro histamine-releasing activity (J. E. Rivier et al., J. Med. Chem. 29, 1846-1851, 1986), but local allergic response in some human subjects remains a concern. Introduction of N$^\epsilon$-nicotinoyl-lysine into positions 5,6 and N$^\epsilon$-isopropyllysine into position 8 led to a compound with high antiovulatory and negligible histamine releasing activity (Ljungqvist et al., Proc. Natl. Acad. Sci. USA, 85 8236-8240, 1988). The modification by Bajusz et al. (Int. J. Pept. Prot. Res., 32 425-435, 1988) i.e. incorporation of citrulline and homocitrulline into position 6 produced peptides having no edematogenic and anaphylactoid side effects and high inhibitory effect, as exemplified by Ac-D-Nal(2)-D-Phe(4Cl)-D-Pal(3)-Ser-Tyr-D-Cit-Leu-Arg-Pro-D-Ala-NH$_2$. Some of these compounds were found to have inhibiting effect on growth of various animal tumor models in vivo and to suppress growth of different human cancer cell lines (A. V. Schally, in General Gynecology, Vol. 6., Parthenon Press, Carnforth, England, 1989, pp. 1-20; Szende et al., J. Natl. Cancer Inst., 82, 513-517, 1990; Szende et al., Cancer Research), 50, 3716-3721, 1990; E. Korkut et al., Proc. Natl. Acad. Sci. US, accepted for publication) and thus might be potential therapeutic agents in the treatment of different cancers (prostate, breast, endometrial, ovarian and pancreatic).

Many human tumors are hormone dependent or hormone-responsive and contain hormone receptors; e.g., mammary carcinomas contain estrogen, progesterone, glucocorticoid, LHRH, EGF, IGF-I. and somatostatin receptors. Peptide hormone receptors have also been detected in acute leukaemia, prostate-, breast-, pancreatic, ovarian-, endometrial cancer, colon cancer and brain tumors (M. N. Pollak, et al., Cancer Lett. 38 223-230, 1987; F. Pekonen, et al., Cancer Res., 48 1343-1347, 1988; M. Fekete, et al., J. Clin. Lab. Anal. 3 137-147, 1989; G. Emons, et al., Eur. J. Cancer Oncol., 25 215-221, 1989). Our recent findings (M. Fekete, et al., Endocrinology, 124 946-955, 1989; M. Fekete, et al. Pancreas 4 521-528, 1989) have revealed that both agonistic and antagonistic analogs of LHRH bind to human breast cancer cell membranes, and also to the cell membranes of pancreatic cancer although the latter tumor thought to be hormone-independent. It has been demonstrated that biologically active peptides such as melanotropin (MSH), epidermal growth factor, insulin and agonistic and antagonistic analogs of LHRH (L. Jennes, et. al., Peptides 5 215-220, 1984) are internalized by their target cells by endocytosis.

SUMMARY OF THE INVENTION

The present invention refers to novel antagonistic decapeptide analogues of hypothalamic LHRH which possess high antiovulatory and antineoplastic activity, and are free of anaphylactoid side effects and are believed to be free of endematogenic effects.

The compounds of this invention are represented by Formula I $$X-R^1-R^2-R^3\text{-Ser-}R^5-R^6(AY_2)\text{-Leu-Arg-Pro-D-Ala-NH}_2 \quad I$$

wherein
$R^1$ is D-Phe, D-Phe(4Cl), D-Nal(1) or D-Nal(2),
$R^2$ is D-Phe or D-Phe(4Hl),
$R^3$ is D-Trp, D-Phe, D-Phe(4Hl), D-Nal(1), D-Nal(2) or D-Pal(3),
$R^5$ is Tyr or Arg,
$R^6$ is D-Lys or D-Orn,
Hl is fluoro, chloro or bromo
X is a lower alkanoyl group of 2-5 carbon atoms,
A is a diaminoacyl residue having the formula $$\begin{array}{c}CH_2-(CH_2)_m-CH-(CH_2)_n-CO-\\ | \quad\quad\quad\quad\quad | \\ NH_2 \quad\quad\quad\quad NH_2\end{array} \quad II$$

where
m is 0 or 1,
n is 0 or 1,
Y is $Y^1$ or $Y^2$, wherein
$Y^1$ is an acyl group derived from straight or branched chain aliphatic or alicyclic carboxylic acids having from 3 to 12 carbon atoms or aromatic carboxylic acid of 6 or 10 ring carbon atoms,
$Y^2$ is a carbamoyl group or $C_1$-$C_5$ alkyl carbamoyl group having the formula $$H-(CH_2)_n-NH-CO- \quad III$$

where n is 0-3.

The therapeutically acceptable salts of the compound of Formula I are included within the scope of this invention.

The peptides of Formula I can be synthesized by classical solution peptide synthesis or preferably, solid phase technique using methylbenzylhydrylamine (MBHA), benzhydrylamine (BAH) resin or 2-methoxy-4-alkoxybenzyl alcohol (Sasrin) resin with a suitable amido linker.

Such method provides intermediate peptides and/or intermediate peptide-resins of Formula IV:

$$X^1-R^1-R^2-R^3-Ser(X^4)-R^5(X^5)-R^6(X^6)\text{-Leu-Arg}(X^8)\text{-Pro-D-Ala-NH}-X^{10} \quad IV$$

wherein
$R^1$, $R^2$, $R^3$, $R^5$, and $R^6$ are as defined above,
$X^1$ is a lower alkanoyl group of 2-5 carbon atoms, $X^4$ is hydrogen or a protecting group for the Ser hydroxyl group,
$X^5$ is hydrogen or a protecting group for the Tyr phenolic hydroxyl group, or a protecting group for the guanidino group of Arg,
$X^6$ is hydrogen or a protecting group for the Lys, Orn,
$X^8$ is hydrogen or a protecting group for the Arg guanidino group,
$X^{10}$ is hydrogen or linking (spacer) group incorporated into a resin.

To insure the selective reactions on the diaminoalkanoyl side chain of $R^6$ to get peptides of Formula I, intermediate peptides of Formula V are prepared by solid phase method as peptides of Formula I with the exception that suitably protected $R^6[A(X^{6'})_2]$ is incorporated in place of $R^6(X^6)$ in position 6:

$$X^1-R^1-R^2-R^3-Ser(X^4)-R^5(X^5)-R^6[A(X^{6'})_2]\text{-Leu-Arg}(X^8)\text{-Pro-D-Ala-NH}-X^{10} \quad V$$

wherein
$X^1$, $R^1$, $R^2$, $R^3$, $R^5$, $R^6$, A are as defined above, $X^1$, $X^4$, $X^5$ and $X^8$ are as defined above but not hydrogen,
$X^{6'}$ is hydrogen or a protecting group of the diamino side chain,
$X^{10}$ is a linkage group incorporated into a resin.

To prepare compounds of Formula I wherein Q is $A(Y^1)_2$ or $A(Y^2)_2$ four different reaction schemes have been utilized:

a) Intermediate peptides of Formula IV (wherein $R^1$, $R^2$, $R^3$, $R^5$, $R^6$ and $X^1$ are as defined above, $X^4$, $X^5$, $X^6$, $X^8$ and $X^{10}$ are hydrogen) are reacted with preformed $A(Y^1)_2$ or $A(Y^2)_2$, wherein A, $Y^1$ and $Y^2$ are defined as above.

b) Alternatively, compounds of Formula V (wherein $R^1$, $R^2$, $R^3$, $R^5$, $R^6$ and $X^1$ are as defined above, $X^4$, $X^5$ are side chain protecting groups, $X^{6'}$ is hydrogen and $X^{10}$ is linkage group of the resin) are used as intermediate peptides. Compounds of Formula I, wherein Y is $Y^1$ produced by direct acylation of intermediate peptide of Formula V with an acyl-halide or -anhydride, followed by splitting the peptides from the resin and removing the protecting groups in one step.

c) According to another method, $R^6[A(Y_2)]$ is prepared in advance by reacting a suitable protected $R^6$ with A then with Y, or with preformed $A(Y)_2$ and followed by incorporation into the peptide during the solid phase peptide synthesis.

d) The two free amino groups of A of intermediate peptides of Formula V (wherein $R^1$, $R^2$, $R^3$, $R^5$, $R^6$, A and $X^1$ are as defined above, $X^4$, $X^5$, $X^{6'}$, $X^8$ and $X^{10}$ are hydrogen) are acylated with acyl-imidazole.

The invention also provides methods for splitting off one or more protecting group(s) and/or cleaving the peptides from the resin support, for purifying a synthesized peptide and converting it into a nontoxic, pharmaceutically acceptable salt, wherein the salts retain the desired biological activity of the parent compound.

The peptides of this invention inhibit the ovulation of female rats at dosages of less 0.15-1.0 μg/kg body weight, when administered s.c. at about noon on the day of proestrus. These peptides have a long acting effect in suppressing the LH, FSH and testosterone levels when they are injected into castrated male rats at doses of 0.5-2.0 micrograms/kg body weight. Peptides 7 and 8 induced significant decrease in the LH levels for more than 24 hours (p<0.01). Forty-eight hours after injection, both antagonists showed significant inhibition (p<0.05) at a dose of 5 μg. At that time, Peptide 8 was active even at a dose of 1.25 μg (p<0.05). The majority of the compounds of Formula I show high affinity for membrane receptors of rat pituitaries and humane breast cancers. In cytotoxicity test, in cultures of human breast and prostate cancer cell lines, some analogues powerfully inhibit the $^3$H-thymidine incorporation.

The inhibition of growth of Dunning R3327H prostate cancer has been demonstrated after treatment of rats with Peptide 8. Tumor doubling time was increased to 42 days comparing to the 12 days of the control group. The body weight did not change during the treatment, however the weight of testis, seminal vesicles and ventral prostate were greatly reduced in the group which received Peptide 8. The results indicated that Peptide 8, released from sustained delivery systems can effectively suppress the growth of prostate cancers.

A pharmaceutical composition is provided by admixing the compound of Formula I with a pharmaceutically acceptable carrier including microcapsules (microspheres) or microgranules (microparticles) formulated from poly(DL-lactide-co-glycolide) for sustained delivery.

DESCRIPTION OF THE PREFERRED EMBODIMENTS

For convenience in describing this invention, the conventional abbreviations for the amino acids, peptides and their derivatives are used as generally accepted in the peptide art and as recommended by the IUPAC-IUB Commission on Biochemical Nomenclature [European. J. Biochem., 138, 9–37 (1984)].

The abbreviations for the individual amino acid residues are based on the trivial name of the amino acid, e.g. pGlu is pyroglutamic acid, His is histidine, Trp is tryptophan, Ser is serine, Tyr is tyrosine, Lys is lysine, Orn is ornithine, Leu is leucine, Arg is arginine, Pro is proline, Gly is glycine, Ala is alanine and Phe is phenylalanine. Where the amino acid residue has isometric forms, it is the L-form of the amino acid that is represented unless otherwise indicated.

Abbreviations of the uncommon amino acids employed in the present invention are as follows: A$_2$pr is 2,3-diaminopropionic acid, A$_2$bu is 2,4-diaminobutyric acid, Nal(2) is 3-(2-naphthyl)alanine, D-Pal(3) is 3-(3-pyridyl)alanine, Phe(4Cl) is 4-chlorophenylalanine.

Peptide sequences are written according to the convention whereby the N-terminal amino acid is on the left and the C-terminal amino acid is on the right.

Other abbreviations used are:
AcOH acetic acid
Ac$_2$O acetic anhydride
Boc tert.butoxycarbonyl
Bz benzoyl
Bzl benzyl
Car Carbamoyl
CHC Cyclohexanoyl
DCB 2,6-dichlorobenzyl
DCC N,N'-dicyclohexylcarbodiimide
DCM dichloromethane
DIC N,N'-diisopropylcarbodiimide
DMF dimethylformamide
EtCar Ethyl Carbamoyl
FMOC Fluorenylmethyloxycarbonyl
HOBt 1-hydroxybenzotriazole
HOPCP pentachlorophenol
HPLC high-performance liquid-chromatography
iPrOH iso-propylalcohol
LAU lauryl
MeCN acetonitrile
MeOH methyl alcohol
OSu N-hydroxy succinamide ester
PRL propionyl
TEA triethylamine
TFA trifluoroacetic acid
Tos 4-toluenesulfonyl
Z(2-Cl) 2-chloro-benzyloxycarbonyl
Z benzyloxycarbonyl Compounds which are especially preferred embodiments of the present invention have the structure:

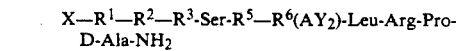

$$X-R^1-R^2-R^3\text{-Ser-}R^5-R^6(AY_2)\text{-Leu-Arg-Pro-D-Ala-NH}_2 \qquad I$$

wherein,
R$^1$ is D-Nal(2);
R$^2$ is D-Phe(4Cl),
R$^3$ is D-Trp or D-Pal(3),
R$^5$ is Tyr or Arg,
R$^6$ is D-Lys or D-Orn,
X is acetyl.
A is A$_2$pr or DL-A$_2$bu,
Y is Y$^1$ or Y$^2$,
wherein
  Y$^1$ is formyl, acetyl, propionyl, butyryl, i-butyryl, cyclohexanoyl or benzoyl,
  Y$^2$ is carbamoyl, N-methyl-carbamoyl or N-ethyl-carbamoyl.

The most particularly preferred embodiments are:
1. Ac-D-Nal(2)-D-Phe(4Cl)-D-Pal(3)-Ser-Arg-D-Lys-[A$_2$pr(Car)$_2$]-Leu-Arg-Pro-D-Ala-NH$_2$,
2. Ac-D-Nal(2)-D-Phe(4Cl)-D-Pal(3)-Ser-Arg-D-Lys-[A$_2$pr(Ac)$_2$]-Leu-Arg-Pro-D-Ala-NH$_2$,
3. Ac-D-Nal(2)-D-Phe(4Cl)-D-Pal(3)-Ser-Arg-D-Lys-[A$_2$pr(For)$_2$]-Leu-Arg-Pro-D-Ala-NH$_2$,
4. Ac-D-Nal(2)-D-Phe(4Cl)-D-Pal(3)-Ser-Arg-D-Lys-[A$_2$pr(EtCar)$_2$]-Leu-Arg-Pro-D-Ala-NH$_2$,
5. Ac-D-Nal(2)-D-Phe(4Cl)-D-Pal(3)-Ser-Arg-D-Lys-[A$_2$pr(CHC)$_2$]-Leu-Arg-Pro-D-Ala-NH$_2$,
6. Ac-D-Nal(2)-D-Phe(4Cl)-D-Pal(3)-Ser-Arg-D-Lys-[A$_2$pr(Bz)$_2$]-Leu-Arg-Pro-D-Ala-NH$_2$,
7. Ac-D-Nal(2)-D-Phe(4Cl)-D-Pal(3)-Ser-Tyr-D-Lys-[A$_2$pr(Car)$_2$]-Leu-Arg-Pro-D-Ala-NH$_2$,
8. Ac-D-Nal(2)-D-Phe(4Cl)-D-Pal(3)-Ser-Tyr-D-Lys-[A$_2$pr(Ac)$_2$]-Leu-Arg-Pro-D-Ala-NH$_2$,
9. Ac-D-Nal(2)-D-Phe(4Cl)-D-Pal(3)-Ser-Tyr-D-Lys-[A$_2$pr(EtCar)$_2$]-Leu-Arg-Pro-D-Ala-NH$_2$,
10. Ac-D-Nal(2)-D-Phe(4Cl)-D-Pal(3)-Ser-Tyr-D-Lys-[A$_2$pr(For)$_2$]-Leu-Arg-Pro-D-Ala-NH$_2$,
11. Ac-D-Nal(2)-D-Phe(4Cl)-D-Pal(3)-Ser-Tyr-D-Lys-[A$_2$pr(PRL)$_2$]-Leu-Arg-Pro-D-Ala-NH$_2$,
12. Ac-D-Nal(2)-D-Phe(4Cl)-D-Pal(3)-Ser-Tyr-D-Lys-[A$_2$pr(CHC)$_2$]-Leu-Arg-Pro-D-Ala-NH$_2$,
13. Ac-D-Nal(2)-D-Phe(4Cl)-D-Pal(3)-Ser-Tyr-D-Lys-[A$_2$pr(Bz)$_2$]-Leu-Arg-Pro-D-Ala-NH$_2$,
14. Ac-D-Nal(2)-D-Phe(4Cl)-D-Pal(3)-Ser-Tyr-D-Lys[DL-A$_2$bu(Ac)$_2$]-Leu-Arg-Pro-D-Ala-NH$_2$,
15. Ac-D-Nal(2)-D-Phe(4Cl)-D-Pal(3)-Ser-Tyr-D-Lys[DL-A$_2$bu(For)$_2$]-Leu-Arg-Pro-D-Ala-NH$_2$,
16. Ac-D-Nal(2)-D-Phe(4Cl)-D-Pal(3)-Ser-Tyr-D-Lys[DL-A$_2$bu(Car)$_2$]-Leu-Arg-Pro-D-Ala-NH$_2$,
17. Ac-D-Nal(2)-D-Phe(4Cl)-D-Pal(3)-Ser-Tyr-D-Lys[DL-A$_2$bu(EtCar)$_2$]-Leu-Arg-Pro-D-Ala-NH$_2$,
18. Ac-D-Nal(2)-D-Phe(4Cl)-D-Pal(3)-Ser-Tyr-D-Lys[DL-A$_2$bu(PRL)$_2$]-Leu-Arg-Pro-D-Ala-NH$_2$, 19. Ac-D-Nal(2)-D-Phe(4Cl)-D-Pal(3)-Ser-Tyr-D-Lys[DL-A$_2$bu(LAU)$_2$]-Leu-Arg-Pro-D-Ala-NH$_2$,
20. Ac-D-Nal(2)-D-Phe(4Cl)-D-Pal(3)-Ser-Tyr-D-Lys[DL-A$_2$bu(Bz)$_2$]-Leu-Arg-Pro-D-Ala-NH$_2$,
21. Ac-D-Nal(2)-D-Phe(4Cl)-D-Pal(3)-Ser-Tyr-D-Lys[DL-A$_2$bu(CHC)$_2$]-Leu-Arg-Pro-D-Ala-NH$_2$,
22. Ac-D-Nal(2)-D-Phe(4Cl)-D-Trp-Ser-Arg-D-Lys-[A$_2$pr(Car)$_2$]-Leu-Arg-Pro-D-Ala-NH$_2$,
23. Ac-D-Nal(2)-D-Phe(4Cl)-D-Trp-Ser-Arg-D-Lys-[A$_2$pr(Ac)$_2$]-Leu-Arg-Pro-D-Ala-NH$_2$,
24. Ac-D-Nal(2)-D-Phe(4Cl)-D-Trp-Ser-Arg-D-Lys-[A$_2$pr(For)$_2$]-Leu-Arg-Pro-D-Ala-NH$_2$,
25. Ac-D-Nal(2)-D-Phe(4Cl)-D-Pal(3)-Ser-Tyr-D-Lys-[A$_2$pr]-Leu-Arg-Pro-D-Ala-NH$_2$,
26. Ac-D-Nal(2)-D-Phe(4Cl)-D-Pal(3)-Ser-Tyr-D-Lys[DL-A$_2$bu]-Leu-Arg-Pro-D-Ala-NH$_2$.

The LHRH antagonizing properties of the compounds of this invention make the compounds useful in human and veterinary practice. For instance, the compounds of Formula I find use as agents for revealing the complications from the undesirable physiological availability of pituitary gonadotropins in a mammal. Such complications include precocious puberty; hormone dependent tumors such as malignant and benign prostate tumors, e.g. secondary amenorrhea; endometriosis and ovarian and mammary cystic diseases in both animals and humans. The compounds of Formula I are also useful for regulating ovulation, thus rendering them useful agents for controlling fertility, e.g. as precoital or postcoital contraceptives, for synchronizing estrus in livestock and for improving the "rhythm" method. Also, the compounds are useful for regulating the human menopausal gonadotropin, follicle-stimulating hormone (FSH) and luteinizing hormone (LH) during perimenopausal and postmenopausal periods in women. As they suppress the spermatogenesis and testosterone level in male they may be potential use for male contraception.

The peptides of the invention are often administered in the form of pharmaceutically acceptable, nontoxic salts, such as acid addition salts. Illustrative of such acid addition salts are hydrochloride, hydrobromide, sulphate, phosphate, fumarate, gluconate, tannate, maleate, acetate, citrate, benzoate, succinate, alginate, pamoate, malate, ascorbate, tartrate, and the like.

Microcapsules or microparticles of these peptides formulated from poly(DL-lactide-co-glycolide) may be the preferred sustained delivery systems. Intravenous administration in isotonic saline, phosphate buffer solutions or the like may be also used.

The pharmaceutical compositions will usually contain the peptide in conjunction with a conventional, pharmaceutically-acceptable carrier. Usually, the dosage, will be from about 1 to 100 micrograms of the peptide per kilogram of the body weight of the host when given intravenously. Overall, treatment of subjects with these peptides is generally carried out in the same manner as the clinical treatment using other agonists and antagonists of LHRH.

These peptides can be administered to mammals intravenously, subcutaneously, intramuscularly, intranasally to achieve LHRH antagonizing and antitumor effect. Effective dosages will vary with the form of administration and the particular species of mammal being treated. An example of one typical dosage form is a physiological saline solution containing the peptide which solution is administered to provide a daily dose in the range of about 0.01 to 0.05 mg/kg of body weight.

Although the invention has been described with regard to its preferred embodiments, it should be understood that changes and modifications obvious to one having the ordinary skill in this art may be made without departing from the scope of the invention, which is set forth in the claims which are appended thereto. Substitutions known in the art which do not significantly detract from its effectiveness may be employed in the invention.

ASSAY PROCEDURES

The compounds of this invention exhibit powerful effect on gonadotropin release by the pituitary, bind to tumor cell membranes and inhibit [$^3$H]thymidine incorporation into DNA in cell cultures.

(a) LH-RH-inhibiting activities

Ability of compounds to influence LH release in vitro is assayed by using a superfused rat pituitary cell system [S. Vigh and A. V. Schally, Peptides, 5 Suppl. 1, 241–247 (1984); V. Csernus and A. V. Schally, in Neuroendocrine Research Methods, Ed. B. Greenstein, Harwood Academic Publishers, London, (1990)].

LHRH inhibiting effect of peptides is assayed as follows: each peptide is perfused through the cells for 9 min (3 ml perfusate) at 1 nM. Immediately after that, a mixture containing the same concentration of peptide and 3 nM LHRH is administered for 3 min. This was followed by four consecutive infusions of 3 nM LHRH for 3 min (1 ml perfusate) at 30 min intervals (30, 60, 90, 120 min). LH content of the 1 ml fractions collected is determined by radioimmunoassay (RIA).

(b) In vivo antiovulatory activity of peptides is determined in 4-day-cycling rats as described [A. Corbin and C. W. Beattie, Endocr. Res. Commun., 2, 1–23 (1975)].

(c) Receptor binding

Affinity of peptides to rat pituitary and human breast cancer cell membranes is determined by using labelled LHRH and [D-Trp$^6$]LHRH. The assay is carried out similarly to that described by T. Kadar et al., Proc. Natl. Acad. Sci. USA, 85, 890–894 (1988) and M. Fekete et al., Endocrinology, 124, 946–955 (1989).

(d) In vivo effect on LH and FSH levels was measured as described by L. Bokser et al. (Proc. Natl. Acad. Sci. US, accepted for publication.) Castrated male rats weighing 350–410 grams anaesthetized with urethane were injected subcutaneously with Peptide 7 and 8 in doses of 1.25 μg and 5.0 μg. Blood samples were taken from the jugular vein before injection and 1, 2, 3, 4, 6, 24 and 48 hours after the administration of peptides. Control animals were injected only with saline. LH and FSH levels were determined by specific RIAs.

(e) Cytotoxicity test

Ability of peptides of Formula I to inhibit incorporation of [$^3$H]thymidine into DNA of monolayer cultures the human mammary tumor cell line MCF-7 is assayed as described [V. K. Sondak et al., Cancer Research, 44, 1725–1728 (1984); F. Holzel et al., J. Cancer Res. Clin. Oncol. 109, 217–226 (1985); M. Albert et al., J. Cancer Res. Clin. Oncol. 109, 210–216 (1985)].

(f) In vivo antitumor effect

Inhibition of growth of cancerous tumors in rats with compounds of Formula I was tested as described by Szende et al. (J. Natl. Cancer Inst., 82, 513–517, 1990; Szende et al., Cancer Research), 50, 3716–3721, 1990) by A. V. Schally and T. Redding (Proc. Natl. Acad. Sci. US, 84, 7279–7282, 1987), and by E. Korkut et al. (Proc. Natl. Acad. Sci. US, accepted for publication). Peptide 8 was dissolved in 45% aqueous propyleneglycol and was administered at a dose of 25 μg/day from an ALZET minipump to male rats bearing the androgen-dependent well-differentiated R3327 Dunning rat prostate adenocarcinoma. Tumors were measured weekly with microcalipers and tumor volumes were calculated. Duration of the treatment was 8 weeks, changing the minipumps at the end of the 4th week.

SYNTHESIS OF PEPTIDES

The peptides of the present invention may be prepared by any techniques that are known to those skilled in the peptide art. A summary of the techniques so available may be found in M. Bodanszky, Principles of Peptide Synthesis, Springer-Verlag, Heildelberg, 1984. Classical solution synthesis is described in detail in the treatise "Methoden der Organische Chemie" (Houben-Weyl), Vol. 15, Synthese von Peptiden, Parts I and II, Georg Thieme Verlag, Stuttgart, 1974. The techniques of exclusively solid-phase synthesis are set forth in the textbook of J. M. Stewart and J. D. Young, Solid Phase Peptide Synthesis, Pierce Chem Co., Rockford, Ill., 1984 (2nd ed.) and in the review of G. Barany, et al., Int. J. Peptide Protein Res. 30, 705–739, 1987.

The basic peptides of this invention were synthesized by solid-phase method, but in some cases the side chain at position 6 were built in by "classical" procedure. In the solid phase synthesis, suitable protected amino acids (sometimes protected peptides) are added stepwise in C→N direction once the C-terminal amino acid has been appropriately attached (anchored) to an inert solid support (resin). After completion of a coupling step, the N-terminal protecting group is removed from this newly added amino acid residue and the next amino acid (suitably protected) is then added, and so forth. After all the desired amino acids have been linked in the proper sequence, the peptide is cleaved from the support and freed from the remaining protecting group(s) under condition that are minimally destructive towards residues in the sequence. This must be followed by a prudent purification and scrupulous characterization of the synthetic product, so as to ensure that the desired structure is indeed the one obtained.

PREFERRED EMBODIMENT OF SYNTHESIS

A particularly preferred method of preparing compounds of Formula I in the present invention is solid phase synthesis, but they can also be synthesized by combining the solid phase and classical (solution) methods. In this particularly preferred method, the α-amino function of the amino acids is protected by an acid or base sensitive group. Such protecting groups should have the properties of being stable to the conditions of peptide linkage formation, while being readily removable without destruction of the growing peptide chain or racemization of any of the chiral centers contained herein.

The peptides of Formula I are preferably prepared from intermediate peptides of Formula IV:

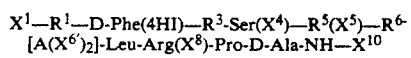

wherein
$R^1$, $R^3$, $R^5$, $R^6$, HI and $X^1$ are as defined hereinabove,
$X^4$ is a protecting group for the hydroxyl group of serine, such as benzyl (Bzl) or 2,6-dichlorobenzyl (DCB). The preferred protecting group is Bzl.

$X^5$ is benzyl, 2-Br-benzyloxycarbonyl or DCB (preferred) to protect the phenolic hydroxyl of $R^5$ Tyr; is Tos (preferred), nitro or methyl-(t-butylbenzene)-sulfonyl to protect the guanidino group if $R^5$ is Arg,
$X^6$ is a protecting group for side chain amino group of Lys or Orn, such as Z, Z(2-Cl) (preferred) or FMOC,
$X^8$ is a protecting group for the Arg and may be nitro, methyl-(t-butylbenzene)sulfonyl or Tos (preferred).
$X^{10}$ is an amide to protect the benzhydryl or methylbenzhydryl group incorporated into resin support; for synthesis of peptide amides, the commercially available benzhydrylamino-polystyrene-2% divinylbenzene copolymer is preferred.

The solid phase synthesis of the peptides of Formula IV is commenced by the attachment of Boc-protected D-Ala to a benzhydrylamine resin in $CH_2Cl_2$. The coupling is carried out using DIC or DIC/HOBt at ambient temperature. After the removal of the Boc group, the coupling of successive protected amino acids (each is applied in a 3 molar excess) is carried out in $CH_2Cl_2$ or in mixtures of $DMF/CH_2Cl_2$ depending on the solubility of Boc-amino acids. The success of coupling reaction at each stage of the synthesis is preferably monitored by the ninhydrin test as described by Kaiser et al. [Anal. Biochem. 34, 595 (1970)]. In cases where incomplete coupling occurs, the coupling procedure is repeated before removal of the alpha-amino protecting group prior to the reaction with the next amino acid.

After the desired amino acid sequence of intermediate peptides of Formula IV has been completed, the N-terminal acetylation is carried out using $Ac_2O$/TEA, and the peptide-resin is then treated with liquid HF in the presence of anisole to yield the peptides of Formula IV wherein $X^4$, $X^5$, $X^6$, $X^8$, and $X^{10}$ are hydrogens.

These peptides are converted into peptides of Formula I (wherein Y is $Y^1$) by carbodiimide coupling method with preformed 2,3-bis-benzoyl-diaminopropionic acid, 2,3-bis-cyclohexanoyl-diaminopropionic acid, 2,3-bis-lauroyl-diaminopropinoic acid, 2,4-bis-benzoyl-diaminobutyric acid, 2,4-bis-cyclohexanoyl-diaminobutyric acid, 2,4-bis-lauroyl-diaminobutyric acid.

To produce compounds of Formula I, wherein $Y^1$ is lower alkanoyl and $Y^2$ is lower carbamoyl, the second synthetic method is preferred because of the high hydrophilicity of the substituents on the lysine[6] side chain, i.e. for example 2,3-bis-formyl-diaminopropionic acid. These kinds of peptides are prepared from compounds of Formula V:

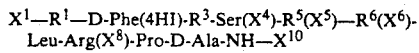

wherein
$R^1$, $R^3$, $R^5$, $R^6$, HI and $X^1$ are as defined hereinabove.
$X^4$ is a protecting group for the hydroxyl group of serine, such as benzyl (Bzl) or 2,6-dichlorobenzyl (DCB). The preferred protecting group is Bzl.
$X^5$ is benzyl, 2-Br-benzyloxycarbonyl or DCB (preferred) for protecting the phenolic hydroxyl of $R^5$ Tyr; or
is Tos (preferred), nitro or methyl-(t-butylbenzene)-sulfonyl to protect the guanidino group if $R^5$ is Arg,
$X^{6'}$ is an amino protecting group for the diaminoacyl side chain of Lys, such as Z, Z(2-Cl) or FMOC,
$X^8$ is suitable for protecting the Arg group; such as nitro, methyl-(t-butylbenzene)-sulfonyl or Tos (preferred), $X^{10}$ is an amide protecting benzhydryl or methylbenzhydryl group incorporated into resin support; for synthesis of peptide amides, the commercially available benzhydrylamino-polystyrene-2% divinylbenzene copolymer is preferred.

Preparation of all protected intermediate peptides of Formula V is carried out by solid phase peptide synthesis, as described for peptides having the Formula IV, but a suitably protected $R^6(A)$ residue, preferably Boc-$R^6[A(FMOC)_2]$, is incorporated in position 6 instead of Boc-$R^6X^6$. The protecting group on A is chosen to be selectively removable, while the other protecting group stay intact during the removal of the two $X^{6'}$. This step can be solved for example by the cleaving FMOC blocking groups with piperidine supplying peptides of Formula Va on resin:

$X^1-R^1-R^2-R^3\text{-Ser}(X^4)\text{-}R^5(X^5)-R^6(A)\text{-Leu-Arg}(X^8)\text{-Pro-D-Ala-NH}-X^{10}$   Va wherein $X^1$, $R^1$, $R^2$, $R^3$, $R^5$, $R^6$ and A are as defined hereinabove, and $X^4$, $X^5$, $X^6$ and $X^{10}$ are not hydrogen.

The free amino groups at position 6 are then acylated with formic acid-$Ac_2O$ mixture, or with halides or anhydride of acetic acid, propionic acid or pivalic acid to give compounds of Formula I, wherein Y is $Y^1$ after deprotection.

Splitting off the protecting groups and cleavage of the peptides from the resin occurred after the formation of the side chain on $R^6$.

In an alternate synthesis, fully deprotected peptides of Formula Vb are obtained by deprotection of intermediate peptides of Formula V in which preferably Boc-$R^6[A(Z)_2]$, incorporated in position 6 instead of Boc-$R^6[A(FMOC)_2]$:

$X^1-R^1-R^2-R^3\text{-Ser-}R^5-R^6(A)\text{-Leu-Arg-Pro-D-Ala-NH}_2$   Vb wherein $X^1$, $R^1$, $R^2$, $R^3$, $R^5$, $R^6$ and A are as defined hereinabove.

The process for producing peptides of Formula I with $A(Y^2)_2$ side chain comprises reacting a peptide of Formula Vb with a source of suitable cyanate, suitably metal-cyanates, e.g. potassium cyanate or an N-alkyl isocyanate, e.g. N-ethyl-isocyanate.

An easy way to produce compounds of Formula I wherein Y is $Y^1$ is the direct acylation of the diamino residue at position 6 of peptides of Formula Vb with equivalent amount of acyl-halide, with $AcO_2$/HCOOH mixture, with acetyl- or propionyl-imidazyl. The reactions are straightforward giving single compounds despite of the presence of free OH group on serine[4].

An alternative synthetic method for preparing peptides of Formula I is incorporating the suitable protected bis-substituted-diaminoacyl-$R^6$ instead of protected $R^6$. The synthesis is carried out exactly as mentioned above except that Boc-$R^6(AY_2)$ is incorporated into the peptide instead of Boc-$R^6(X^6)$ at the fifth step of the synthesis.

Purification of Peptides

Crude synthetic products (>500 mg) were purified on a BECKMAN Prep-350 preparative HPLC system equipped with a DYNAMAX MACRO column (41.4×250 mm) packed with spherical C18 silica gel (pore size: 300 Å, particle size: 12 μm) (RAININ Inc., Co., Woburn, Mass.) (Column A). Purification of smaller amount of peptides (<250 mg) were performed on a BECKMAN HPLC system (Model 142) using a DYNAMAX MACRO (21.2×250 mm) column packed with the same medium, as above (Column B). To purify peptides weighing <50 mg, a reversed phase, 10×250 mm VYDAC Protein & Peptide $C_{18}$ column (pore size: 300 Å, particle size: 5 μm) (ALTECH, Deerfield, Ill.) (Column C) or a 10×250 mm W-POREX $C_{18}$ column (pore size: 300 Å, particle size: μm) (Phenomenex, Rancho Palos Verdes, Calif.) (Column D) were used. Columns were eluted with solvent system i consisting of (A) 0.1% aqueous TFA and (B) 0.1% TFA in 70% aqueous acetonitrile usually in a gradient mode. Column eluant was monitored with UV detectors operating at 230 or 280 nm. Chromatography was effected at ambient temperature.

Analytical HPLC

Analysis of crude and purified peptides was carried out with a Hewlett-Packard Model 1090 liquid chromatograph equipped with a diode array detector set for 220 and 280 nm and a reversed phase 4.6×250 mm W-POREX $C_{18}$ column (pore size: 300 Å, particle size: 5 μm) (Column E). A flow rate of 1.2 ml/min of solvent system i or solvent system ii consisting of (A) 0.05M ammoniumacetate pH=7.0 and (B) 0.05M ammoniumacetate in 65% aqueous acetonitrile was maintained and the separations were performed at room temperature.

Amino Acid Analysis

Peptide samples are hydrolized at 110° C. for 20 hr in evacuated sealed tubes containing 4M methane-sulfonic acid. Analysis are performed with a Beckman 6300 amino acid analyzer.

PREPARATION I

| | |
|---|---|
| bis-benzoyl-2,4-diaminopropionic acid | Ia |
| bis-benzoyl-2,4-DL-diaminobutyric acid | Ib |

To the solution of 140 mg (1 mmol) DL-$A_2$pr in 2 ml 10% NaOH, 1.5 ml of 25% benzoylchloride in dioxane was added in dropwise at 4° C. The reaction mixture was mixed for 24 hours at 4° C. then the title compound was extracted with ethylacetate and purified by recrystallization from chloroform-hexane. $(Bz)_2$-DL-$A_2$bu was prepared similarly but using DL-$A_2$bu instead of $A_2$pr. Retention factors are 0.60 and 0.69, respectively, on silicagel TLC plate with solvent system ethylacetate-pyridine-acetic acid-water 60-20-6-11.

PREPARATION II

| | |
|---|---|
| bis-cyclohexanoyl-2,3-diaminopropionic acid | IIa |
| bis-cyclohexanoyl-2,3-DL-diaminobutyric acid | IIb |

140 mg (1 mmol) DL-$A_2$pr.HCl in 2 ml of 10% NaOH was stirred for 24 hours at room temperature with 1.6 ml (3 mmol) 25% cyclohexanecarbonyl chloride in dioxane added by dropwise. The title compound was purified by solvent extraction and recrystallized from benzene-hexane.

Preparation IIb was made in a similar manner except using 191 mg (1 mmol) DL-2,4-diaminobutyric acid.2HCl instead of 2,3-diaminopropionic acid. The retention factors are 0.69 and 0.79, when chromatographed on silicagel TLC in solvent system as described in preparation I.

PREPARATION III

Boc-D-Lys(A₂pr)-OH      IIIa

Boc-D-Lys(DL-A₂bu)-OH      IIIb

To a DMF solution (4 ml) of a mixed anhydride, prepared from $Z_2$-$A_2$pr (0.72 g) and ethyl-chloroformate (0.2 ml) in the presence of TEA (0.28 ml), 4 ml DMF containing 0.5 g $N^\alpha$-Boc-D-Lys and 0.3 ml TEA were added with stirring at 0° C. After two hours, the reaction mixture was concentrated to an oil under reduced pressure, dissolved in water and ethylacetate and acidified with 1M KHSO₄. The organic phase was washed with water, dried over Na₂SO₄ and evaporated under vacuum. 0.5 g of this protected dipeptide was dissolved in 25 ml 50% aqueous acetic acid and hydrogenated at room temperature for 2 hours in the presence of 0.1 g Pd/C (10%). The reaction mixture was filtered and evaporated to dryness. The resulting white product was rubbed with diethylether, filtered and dried.

Preparation IIIb was prepared in a similar manner but acylating with $Z_2$-DL-$A_2$bu instead of $Z_2$-$A_2$pr.

PREPARATION IV (FMOC)₂A₂pr-OH 0.5 g (3.55 mmol) 2,3-diaminopropionic acid was dissolved in 7.1 ml N NaOH and 2.75 g (15% excess) FMOC-OSu in 25 ml acetone was added dropwise while stirring the mixture at room temperature. After 4 hours stirring, 3.55 ml N H₂SO₄ was added, the reaction mixture was filtered, washed with 3×10 ml water and air-dried on the funnel. The product was recrystallized from ethylacetate-petroleum ether. The purity of the white precipitate (weighted 1.9 g) was checked on silica gel TLC with the following solvent system: ethylacetate-pyridine-acetic acid-water = 120:20:6:11 ($R_f$ = 0.62–0.66).

PREPARATION V

Boc-D-Lys[(FMOC)₂A₂pr]—OH 0.73 g (3 mmol) $N^\alpha$-Boc-D-Lys-OH was suspended with 0.42 ml (3 mmol) TEA in 3 ml 50% aqueous DMF. Then 1.8 g (3.2 mmol) (FMOC)₂A₂pr (Preparation VIII) and 0.37 g HOBt was dissolved in 3 ml DMF and was mixed with 0.5 ml DIC at 0° C. After 10 min this solution was added to the Boc-D-Lys-OH suspension. On stirring at room temperature, the reaction mixture became clear in 1 hour. Pouring the mixture into 30 ml water, yielded a yellowish voluminous precipitate which crystallized by rubbing with diethyl ether and recrystallized from MeOH-DCM-hexane solution (1.2 g). The title compound proved to be homogeneous on silicagel TLC ($R_f$ = 0.68–0.72) developed with solvent system ethylacetate-pyridine-acetic acid-water 960:20:6:11.

PREPARATION VI

Ac-D-Nal(2)-D-Phe(4Cl)-D-Pal(3)-Ser-Tyr-D-Lys-
    Leu-Arg-Pro-D-Ala-NH₂      VIa

Ac-D-Nal(2)-D-Phe(4Cl)-D-Pal(3)-Ser-Arg-D-Lys-
    Leu-Arg-Pro-D-Ala-NH₂      VIb

Ac-D-Nal(2)-D-Phe(4Cl)-D-Trp-Ser-Arg-D-Lys-
    Leu-Arg-Pro-D-Ala-NH₂      VIc

Boc-D-Ala was attached to 1 g (about 1 mmol) neutralized benzhydrylamine resin containing 1 meq NH₂ (Advanced Chemtech, Louisville, Ky.) by means of N,N'-diisopropylcarbodiimide (DIC)/1-hydroxybenztriazole (HOBt) mediated coupling for about 2 hours at room temperature in dichloromethane or DMF. The coupling of successive protected amino acids were carried out in a reaction vessel for manual solid phase synthesis using 2.5–3.0 molar excess of protected amino acids in accordance with the scedule as follows:

| STEP | REAGENTS AND OPERATIONS | MIXING TIMES (Min) |
|---|---|---|
| 1 | Coupling: Boc-amino acid in DCM or DMF depending on the solubility of the particular protected amino acid, plus DIC | 60–90 |
| 2 | iPrOH (or DME then iPOH) wash | 2 |
| 3 | DCM wash | 2 |
| 4 | iPrOH wash | 2 |
| 5 | DCM wash (three times) | 2 |
| 6 | Deprotection: 50% TFA in DCM twice) | 5 and 25 |
| 7 | DCM wash | 2 |
| 8 | iPrOH wash | 1 |
| 9 | Neutralization: 10% TEA in DCM | 2 |
| 10 | iPrOH wash | 1 |
| 11 | Neutralization: 10% TEA in DCM | 2 |
| 12 | iPrOH wash | 1 |
| 13 | DCM wash (three times) | 2 |

After attaching Boc-Ala to the resin, the following amino acids were then coupled successively by the same cycle of events: Boc-Pro, Boc-Arg(Tos), Boc-Leu, Boc-D-Lys[Z(2-Cl)], Boc-Tyr(Bzl), Boc-Ser(Bzl), Boc-D-Pal(3), Boc-D-Phe(4Cl), and Boc-D-Nal(2).

Using Boc-Arg(Tos) instead of Boc-Tyr(Bzl) leads to the peptide resin having the structure of Boc-D-Nal(2)-D-Phe(4Cl)-D-Pal(3)-Ser(Bzl)-Arg(Tos)-D-Lys[Zl-(2-Cl)]-Leu-Arg(Tos)-Pro-D-Ala-NH-RESIN. Likewise, changing Boc-D-Pal(3) to D-Trp in position 3 resulted in the peptide-resin Boc-D-Nal(2)-D-Phe(4Cl)-D-Trp-Ser(Bzl)-Arg(Tos)-D-Lys[Zl-(2Cl)]-Leu-Arg(Tos)-Pro-D-Ala-NH-RESIN.

The decapeptide-resin (3–3.5 g) containing free N-terminal amino group was treated with 50-fold excess acetic anhydride and TEA in 30 ml of DMF for 30 min. The acetylated peptide-resin then was washed with DMF (3 times), iPrOH (3 times) and DCM (3 times) and dried in vacuo. Removal of the protecting groups and cleavage of the decapeptide from the resin was carried out by treatment of 1.5–2 g of material with liquid HF (30 ml), anisole (3 ml) at 0 C. for 45 min. The hydrogen fluoride was eliminated under a stream of nitrogen and the peptide was precipitated by addition of diethylether. The peptide was then extracted with 50% aqueous acetic acid (3 times), separated from the resin by filtration, diluted with water and lyophilized.

Crude peptides were purified on Column A with solvent system i using a linear gradient of 40–70% B in 60 min for Preparation VIa and 20–60% B in 80 min for Preparation VIb and VIc. HPLC retention times of Preparation VIa (837 mg), VIb (540 mg) and VIc (521 mg) are 25.5 min, 11.4 min and 18.8 min, respectively, when using solvent system i in linear gradient mode (30–60% B in 30 min). Amino acid analysis gave the expected results.

PREPARATION VII

Ac-D-Nal(2)-D-Phe(4Cl)-D-Pal(3)-Ser(Bzl)-
Tyr(Bzl)-D-Lys($A_2$pr)-Leu-Arg(Tos)-Pro-D-Ala-
NH-resin     VIIa Ac-D-Nal(2)-D-Phe(4Cl)-D-Pal(3)-Ser(Bzl)-
Arg(Tos)-D-Lys($A_2$pr)-Leu-Arg(Tos)-Pro-D-
Ala-NH-resin     VIIb Ac-D-Nal(2)-D-Phe(4Cl)-D-Trp-Ser(Bzl)-Arg(Tos)-
D-Lys($A_2$pr)-Leu-Arg(Tos)-Pro-D-Ala-NH-resin     VIIc Preparation of VIIa is carried out by solid phase peptide synthesis in accordance with the procedures set forth in the schedule of Preparation VI. The decapeptide is built up in ten successive steps coupling Boc-D-Ala to 1 g benzhydrylamine resin first, followed by Boc-Pro, Boc-Arg(Tos), Boc-Leu, Boc-D-Lys[$A_2$pr(FMOC)], Boc-Tyr(Bzl), Boc-Ser(Bzl)Boc-D-Pal(3), Boc-D-Phe(4Cl) and Boc-D-Nal(2). N-Terminal acetylation is performed with a 50-fold excess of acetic anhydride in DMF for 30 min. FMOC protecting groups on $A_2$pr were removed by treating the peptide resin with 20 ml 50% piperidine in DMF for 18 h and the washed with DMF (3 times), iPrOH (3 times) and DCM (3 times) and kept in a desiccator till the next reaction.

Proceeding in a similar manner but incorporating Boc-Arg(Tos) in place of Boc-Tyr(Bzl) at position 5, Ac-D-Nal(2)-D-Phe(4Cl)-D-Pal(3)-Ser(Bzl)-Arg(Tos)-D-Lys($A_2$pr)-Leu-Arg(Tos)-Pro-D-Ala-NH-resin(-Preparation VIIb) is prepared. Using Boc-D-Trp instead of Boc-D-Pal(3) at position 3 and Boc-Arg(Tos) instead of Boc-Tyr(Bzl) at position 5 results in Ac-D-Nal(2)-D-Phe(4Cl)-D-Trp-Ser(Bzl)-Arg(Tos)-D-Lys-($A_2$pr)-Leu-Arg(Tos)-Pro-D-Ala-NH-resin (Preparation VIIc).

PREPARATION VIII

Ac-D-Nal(2)-D-Phe(4Cl)-D-Pal(3)-Ser-Tyr-D-Lys-
($A_2$pr)-Leu-Arg-Pro-D-Ala-NH$_2$     VIIIa

Ac-D-Nal(2)-D-Phe(4Cl)-D-Pal(3)-Ser-Arg-D-Lys-
($A_2$pr)-Leu-Arg-Pro-D-Ala-NH$_2$     VIIIb

Ac-Nal(2)-D-Phe(4Cl)-D-Trp-Ser-Arg-D-Lys-
($A_2$pr)-Leu-Arg-Pro-D-Ala-NH$_2$     VIIIc

The peptides of VIIIa, VIIIb and VIIIc were prepared by the solid-phase technique on benzhydrylamine HCl resin in accordance with the procedures set forth in the Schedule of Preparation VI.

Thus, the resin (0.5 g containing about 0.5 mmole NH$_2$) is treated during the ten successive coupling cycles with Boc-D-Ala, Boc-Pro, Boc-Arg(Tos), Boc-Leu, Boc-Lys[$A_2$pr(Z)$_2$], Boc-Tyr(Bzl), Boc-Ser(Bzl), Boc-D-Pal(3), Boc-D-Phe(4Cl), Boc-D-Nal(2) and finally with Ac$_2$O/imidazole to yield a peptide-resin which is then treated with HF and anisole to afford the free, D-Lys($A_2$pr)-containing peptide of VIIIa.

Proceeding in a similar manner but incorporating Boc-D-Trp in place of Boc-D-Pal(3) at position 3, the free, D-Lys($A_2$pr)-containing peptide of VIIIc was prepared (500 mg).

Alternatively, Preparation VIIIa, VIIIb and VIIIc are obtained from Preparation VIa, VIb and VIc by acylation with Boc$_2$-$A_2$pr in carbodiimide reaction in the presence of HOBt. Boc groups are then removed by treatment with 50% TFA in DCM, the peptide was precipitated with diethyl-ether, filtered and dried in vacuo.

Crude peptides were purified on Column A with a gradient of solvent system i (20–60% B in 80 min). HPLC retention times of VIIIa, VIIIb and VIIIc are 15.1 min, 10.1 min and 17.5 min, respectively, when using solvent system i in a linear gradient mode (30–50% B in min).

PREPARATION IX

Ac-D-Nal(2)-D-Phe(4Cl)-D-Pal(3)-Ser-Tyr-D-
Lys(DL-$A_2$bu)-Leu-Arg-Pro-D-Ala-NH$_2$

Preparation IX is prepared by solid phase peptide synthesis as decribed for Preparation VIIIA with the exception that Boc-D-Lys[DL-$A_2$bu(Z)$_2$] is built into the peptide chain in position 6 instead of Boc-D-Lys-[$A_2$pr(Z)$_2$]. HPLC retention time of Preparation IX is 10.4 min when using solvent system i in a linear gradient mode (35–50% B in 15 min).

EXAMPLE 1

The peptide Ac-D-Nal(2)-D-Phe(4Cl)-D-Pal(3)-Ser-Tyr-D-Lys[$A_2$pr(Ac)$_2$]-Leu-Arg-Pro-D-Ala-NH$_2$ (8) was prepared on solid phase by acetylating the free amino groups on $A_2$pr substituted Lys side chain of Preparation VII (0.3 g) with 470 μl acetyl-imidazole in the presence of 700 μl TEA. The peptide was then deprotected and split from the resin in one step using liquid HF as described for Preparation VI. The crude peptide was purified by HPLC on Column B eluted with solvent system i using linear gradient (25–50% B in 45 min).

EXAMPLE 2

The syntheses of Ac-D-Nal(2)-D-Phe(4Cl)-D-Pal(3)-Ser-Arg-D-Lys[$A_2$pr(Bz)$_2$-Leu-Arg-Pro-D-Ala-NH$_2$ (13) and Ac-D-Nal(2)-D-Phe(4Cl)-D-Pal(3)-Ser-Arg-D-Lys[$A_2$pr(Bz)$_2$]-Leu-Arg-Pro-D-Ala-NH$_2$ (6) were accomplished by the coupling of Preparation VIb and 2,3-bis-benzoyl-diaminopropionic acid (Preparation Ia) with carbodiimide. A solution (200 μl DMF) of 7 mg Preparation Ia and 3.1 mg HOBt was cooled to 0° C. then reacted with 3.5 μl DIC for 15 min. 36.3 mg Preparation VIb dissolved in 200 μl DMF, neutralized with TEA and mixed with the above prepared active ester solution and kept at 0° C. for 18 hours. The reaction mixture was directly injected onto the Column C and purified by eluting with solvent system i to afford compound 13 (17.6 mg) and 6 (18 mg), respectively.

Following the same procedure, but acylating Preparation VIb and VIc with $A_2$pr(AC)$_2$, Ac-D-Nal(2)-D-Phe(4Cl)-D-Pal(3)-Ser-Arg-D-Lys[($A_2$pr(Ac)$_2$]-Leu-Arg-Pro-D-Ala-NH$_2$ (2) (19.1 mg) and Ac-D-Nal(2)-D-Phe(4Cl)-D-Trp-Ser-Arg-D-Lys[$A_2$pr(Ac)$_2$]-Leu-Arg-Pro-D-Ala-NH$_2$ (23) (17.2 mg) were prepared.

Acylating Preparation VIb and Via with 2,3-bis-cyclohexanoyl-diminopriopionic acid (Preparation IIa) gave 14.8 mg Ac-D-Nal(2)-D-Phe(4Cl)-D-Pal(3)-Ser-Arg-D-Lys[$A_2$pr(CHC)$_2$]-Leu-Arg-Pro-D-Ala-NH$_2$ (5) and 15.3 mg Ac-D-Nal(2)-D-Phe(4Cl)-D-Pal(3)-Ser-Tyr-D-Lys[$A_2$pr(CHC)$_2$]-Leu-Arg-Pro-D-Ala-NH$_2$ (12). respectively.

Reacting Preparation VIa with 2,4-bis-benzoyl-diaminobutyric acid (Preparation Ib) with 2,4-bis-cyclohexanoyl-diaminobutyric acid (Preparation IIb) or with 2,4-bis-lauroyl-diaminobutyric acid resulted respectively in peptides Ac-D-Nal(2)-D-Phe(4Cl)-D-

Pal(3)-Ser-Tyr-D-Lys[DL-A₂bu(Bz)₂]-Leu-Arg-Pro-D-Ala-NH₂ (20) (16.6 mg), Ac-D-Nal(2)-D-Phe(4Cl)-D-Pal(3)-Ser-Tyr-D-Lys[DL-A₂bu(CHC)₂]-Leu-Arg-Pro-D-Ala-NH₂ (21) (14.7 mg) and Ac-D-Nal(2)-D-Phe(4Cl)-D-Pal(3)-Ser-Tyr-D-Lys[DL-A₂bu(LAU)₂]-Leu-Arg-Pro-D-Ala-NH₂ (19) (8 mg), respectively.

EXAMPLE 3

The synthesis of Ac-D-Nal(2)-D-Phe(4Cl)-D-Pal(3)-Ser-Tyr-D-Lys[DL-A₂bu(Car)₂]-Leu-Arg-Pro-D-Ala-NH₂ (16) was carried out by carbamylating the two free amino group containing intermediate peptide (Preparation IX). 37 mg Preparation IX was dissolved in 100 μl DMF and the solution buffered by addition of 15 μl TEA and 30 μl acetic acid. To this mixture, solution of 48 mg potassium cyanate in 100 μl water was added and the reaction kept at ambient temperature for 48 hours. The title peptide (15.8 mg) was isolated by HPLC purification on Column C using solvent system i.

Proceeding in a similar manner but using Preparations VIIIa, VIIIb and VIIIc as precursor, the following peptides were prepared: Ac-D-Nal(2)-D-Phe(4Cl)-D-Pal(3)-Ser-Tyr-D-Lys[A₂pr(Car)₂]-Leu-Arg-Pro-D-Ala-NH₂ (7) (12.2 mg), Ac-D-Nal(2)-D-Phe(4Cl)-D-Pal(3)-Ser-Arg-D-Lys[A₂pr(Car)₂]-Leu-Arg-Pro-D-Ala-NH₂ (1) (14.7 mg) and Ac-D-Nal(2)-D-Phe(4Cl)-D-Trp-Ser-Arg-D-Lys[A₂pr(Car)₂]-Leu-Arg-Pro-D-Ala-NH₂ (22) (11.2 mg).

EXAMPLE 4

Ac-D-Nal(2)-D-Phe(4Cl)-D-Pal(3)-Ser-Tyr-D-Lys[DL-A₂bu(PRL)₂]-Leu-Arg-Pro-D-Ala-NH₂ (18) was prepared by propionylation of the two free amino groups on the substituted Lys side chain of Preparation IX. 37 mg intermediate peptide was dissolved in 100 μl DMF, neutralized with 7 μl TEA and reacted with 50 μl preformed propionyl-imidazole reagent for 24 hours at room temperature. The reaction mixture was subjected to HPLC on Column C eluted with solvent system i. Lyophilized fractions containing pure peptide yielded 13 mg of the title peptide.

Compounds Ac-D-Nal(2)-D-Phe(4Cl)-D-Pal(3)-Ser-Tyr-D-Lys[A₂pr(Ac)₂]-Leu-Arg-Pro-D-Ala-NH₂ (8) (14.1 mg) and Ac-D-Nal(2)-D-Phe(4Cl)-D-Pal(3)-Ser-Tyr-D-Lys[DL-A₂bu(Ac)₂]-Leu-Arg-Pro-D-Ala-NH₂ (14) (12.8 mg) were prepared by the method described in this example but using Preparation VIIIa and Preparation IX as a starting compound, respectively, and acetyl-imidazole as an acylating agent.

EXAMPLE 5

The peptide Ac-D-Nal(2)-D-Phe(4Cl)-D-Pal(3)-Ser-Tyr-D-Lys[A₂pr(PRL)₂]-Leu-Arg-Pro-D-Ala-NH₂ (11) was synthesized by solid phase peptide synthesis on benzhydrylamine resin (1 g≈1 mmol), as described for Preparation VI. The decapeptide was built up by successive coupling of the following protected amino acids (or derivatives): Boc-Ala, Boc-Pro, Boc-Arg(Tos), Boc-Leu, Boc-D-Lys[A₂pr(PRL)₂], Boc-Tyr(Bzl), Boc-Ser(Bzl), Boc-D-Pal(3), Boc-D-Phe(4Cl) and Boc-D-Nal(2). After acetylation of the N-terminal amino group, removal of the protecting groups and cleavage of the decapeptide from the resin were carried out as described for Preparation VI. The crude, lyophilized peptide was purified on Column C.

EXAMPLE 6

The synthesis of Ac-D-Nal(2)-D-Phe(4Cl)-D-Pal(3)-Ser-Arg-D-Lys[A₂pr(For)₂]-Leu-Arg-Pro-D-Ala-NH₂ (3) was carried out by formylation of free amino groups of an intermediate peptide (VIIIa) with preformed mixed anhydride from formic acid and acetic anhydride. To prepare this anhydride, 960 μl (10 mmole) acetic anhydride was left to react with 390 μl (10 mmole) formic acid at 0° C. for 30 min. 37 mg Preparation VIIIa was dissolved in 100 μl DMF, 7 μl TEA and 6.7 μl (50 μmole) of above prepared reagent was added and the mixture was kept at 0° C. for 1 hour. Purification of Peptide 3 was achieved by HPLC on Column C eluted with solvent system i and the yield was 22.8 mg.

Peptides Ac-D-Nal(2)-D-Phe(4Cl)-D-Pal(3)-Ser-Tyr-D-Tyr-D-Lys[A₃pr(For)₂]Leu-Arg-Pro-D-Ala-NH₂ (10), Ac-D-Nal(2)-D-Phe(4Cl)-D-Pal(3)-Ser-Tyr-D-Lys[DL-A₂bu(For)₂]-Leu-Arg-Pro-D-Ala-NH₂ (15) and Ac-D-Nal(2)-D-Phe(4Cl)-D-Trp-Ser-Arg-D-Lys[A₂pr(For)₂]Leu-Arg-Pro-D-Ala-NH₂ (24) were synthesized in the same way with the exception that Ac-D-Nal(2)-D-Phe(4Cl)-D-Pal(3)-Ser-Tyr-D-Lys(A₂pr)-Leu-Arg-Pro-D-Ala-NH₂ (Preparation VIIIa), Ac-D-Nal(2)-D-Phe-(4Cl)-D-Pal(3)-Ser-Tyr-D-Lys(DL-A₂bu)-Leu-Arg-Pro-D-Ala-NH₂ (Preparation IX) and Ac-D-Nal(2)-D-Phe(4Cl)-D-Trp-Ser-Arg-D-Lys-A₂pr)-Leu-Arg-Pro-D-Ala-NH₂ (Preparation VIIIc) were used as starting compounds.

EXAMPLE 7

The synthesis of the peptide Ac-D-Nal(2)-D-Phe(4Cl)-D-Pal(3)-Ser-Arg-D-Lys[A₂pr(EtCar)₂]-Leu-Arg-Pro-D-Ala-NH₂ was accomplished by reacting intermediate peptide Ac-D-Nal(2)-D-Phe(4Cl)-D-Pal(3)-Ser-Arg-D-Lys(A₂pr)-Leu-Arg-Pro-D-Ala-NH₂ (Preparation VIIIb) with N-ethylisocyanate. 36 mg (20 μmole) at intermediate peptide dissolved in 100 μl DMF, pH was adjusted with 14 μl (100 μmole) TEA and the peptide was reacted with 3.5 μl N-ethylisocyanate at 0° C. for 10 hours. The reaction mixture was injected onto Column C and eluted with solvent system i to afford the desired peptide (21.8 mg).

The syntheses of Ac-D-Nal(2)-D-Phe(4Cl)-D-Pal(3)-Ser-Tyr-D-Lys[A₂pr(EtCar)₂]-Leu-Arg-Pro-D-Ala-NH₂ (9) and Ac-D-Nal(2)-D-Phe(4Cl)-D-Pal(3)-Ser-Tyr-D-Lys[DL-A₂bu(EtCar)₂]-Leu-Arg-Pro-D-Ala-NH₂ (17) were accomplished by the same manner but using Ac-D-Nal(2)-D-Phe-(4Cl)-D-Pal(3)-Ser-Tyr-D-Lys(A₂pr)-Leu-Arg-Pro-D-Ala-NH₂(Preparation VIIIa) and Ac-D-Nal(2)-D-Phe (4Cl)-D-Pal(3)-Ser-Tyr-D-Lys(DL-A₂bu)-Leu-Ar-g-Pro-D-Ala-NH₂ (Preparation IX), respectively.

TABLE 1

Preparation and HPLC purification methods for LH-RH antagonist

| No. of Peptide | Synthetic method | Gradient (% B/min) for purification | Gradient (% B/min) for analysis | Retention time (min) |
|---|---|---|---|---|
| 1. | 3 | 25–50/40 | 30–45/15 | 12.5 |
| 2. | 2 | 30–45/45 | 35–50/15 | 10.0 |
| 3. | 6 | 20–50/50 | 35–50/15 | 8.7 |
| 4. | 7 | 25–45/50 | 35–50/15 | 11.0 |
| 5. | 2 | 30–55/50 | 45–60/15 | 12.0 |
| 6. | 2 | 35–55/60 | 45–60/15 | 9.5 |
| 7. | 3 | 30–60/60 | 35–50/15 | 8.2 |
| 8. | 1 & 4 | 25–50/50 | 35–50/15 | 12.5 |
| 9. | 7 | 25–45/50 | 40–55/15 | 10.6 |
| 10. | 6 | 30–45/45 | 35–50/15 | 10.3 |
| 11. | 4 | 30–55/50 | 35–50/15 | 14.8 |

TABLE 1-continued

Preparation and HPLC purification methods for LH-RH antagonist

| No. of Peptide | Synthetic method | Gradient (% B/min) for purification | Gradient (% B/min) for analysis | Retention time (min) |
|---|---|---|---|---|
| 12. | 2 | 25–45/50 | 55–70/15 | 11.9 |
| 13. | 2 | 25–45/50 | 35–50/15 | 12.3 |
| 14. | 4 | 25–45/50 | 35–50/15 | 12.8 |
| 15. | 6 | 25–40/45 | 35–50/15 | 12.3 |
| 16. | 3 | 35–50/45 | 35–50/15 | 11.8 |
| 17. | 7 | 25–50/50 | 35–50/15 | 13.9 |
| 18. | 4 | 30–50/40 | 35–65/15 | 14.7 |
| 19. | 2 | 50–90/60 | 80–95/15 | 12.0 |
| 20. | 2 | 35–50/45 | 45–60/15 | 8.0 |
| 21. | 2 | 50–80/60 | 50–65/15 | 10.9 |
| 22. | 3 | 30–50/40 | 45–60/15 | 8.0 |
| 23. | 2 | 35–55/40 | 45–60/15 | 9.3 |
| 24. | 6 | 35–55/40 | 40–55/15 | 12.0 |
| 25. | Prep. VIIIa | 20–50/60 | 35–50/15 | 9.3 |
| 26. | Prep. IX | 20–50/60 | 35–50/15 | 9.1 |

TABLE 2

Antiovulatory activity and affinity of Ac—D—Nal(2)—D—Phe(4Cl)—$R^3$—Ser—Arg—D—Lys[$A_2$pr(Y)$_2$]—Leu—Arg—Pro—D—Ala—NH$_2$ peptides for membrane receptors of human breast cancer cells

| No. of Peptide | $R^3$ | Y | % Blockade of Ovulation 0.75 μg | % Blockade of Ovulation 1.5 μg | Affinity Constant $K_a1$ nM$^{-1}$ | Affinity Constant $K_a2$ uM$^{-1}$ |
|---|---|---|---|---|---|---|
| 1 | D-Pal(3) | Car | | | 7.07 | 3.15 |
| 2 | D-Pal(3) | Ac | | | 16.35 | 0.32 |
| 3 | D-Pal(3) | For | | | NB | |
| 4 | D-Pal(3) | EtCar | | | 9.71 | 0.05 |
| 5 | D-Pal(3) | CHC | | 40 | NB | |
| 6 | D-Pal(3) | BZ | 10 | 20 | NB | |
| 22 | D-Trp | Car | | | 4.09 | 2.67 |
| 23 | D-Trp | Ac | | | 6.87 | 0.14 |
| 24 | D-Trp | For | | 50 | NB | |

*$^{125}$I-[D-Trp]$^6$LHRH used as the labelled ligand
NB, no binding

TABLE 3

Antiovulatory activity and affinity of Ac—D—Nal(2)—D—Phe(4Cl)—D—Pal(3)—Ser—Arg—D—Lys[A(Y)$_2$]Leu—Arg—Pro—D—Ala—NH$_2$ peptides for membrane receptors of human breast cancer cells

| No. of Peptide | A | Y | % Blockade of Ovulation 0.75 μg | % Blockade of Ovulation 1.5 μg | Affinity Constant $K_a1$ nM$^{-1}$ | Affinity Constant $K_a2$ uM$^{-1}$ |
|---|---|---|---|---|---|---|
| 7 | $A_2$pr | Car | | | 6.27 | 5.72 |
| 8 | $A_2$pr | Ac | | | 1.57 | 6.16 |
| 9 | $A_2$pr | EtCar | 20 | 50 | 30.92 | 8.57 |
| 10 | $A_2$pr | For | 67 | 100 | 48.29 | 2.11 |
| 12 | $A_2$pr | CHC | | | 1.68 | 3.57 |
| 14 | DL-$A_2$bu | Ac | | 20 | 4.83 | 0.28 |
| 15 | DL-$A_2$bu | For | (25**) | 100 | NB | |
| 16 | DL-$A_2$bu | Car | | 33 | NB | |
| 18 | DL-$A_2$bu | PRL | 75 | | 21.18 | 6.17 |
| 19 | DL-$A_2$bu | LAU | | | 0 | 0 |
| 21 | DL-$A_2$bu | CHC | | | NB | |
| 25 | $A_2$pr- | | | | 3.49 | 1.29 |
| 26 | DL-$A_2$bu- | | | | NB | |

*$^{125}$I-[D-Trp]$^6$LHRH used as the labelled ligand
**dose is 0.375 μg
NB, no binding

TABLE 4

LH-RH inhibiting activities of Ac—D—Nal(2)—D—Phe(4Cl)—$R^3$—Ser—Arg—D—Lys[$A_2$pr(Y)$_2$]—Leu—Arg—Pro—D—Ala—NH$_2$ antagonists in perfused rat pituitary cell system at various molar ratios of antagonist to LH-RH

| | % inhibition of LH response at different antagonist to LH-RH ratio | | | | | | | |
|---|---|---|---|---|---|---|---|---|
| | 1:1 | | | | 3:1 | | | |
| No. of Peptide | 0 min | 30 min | 60 min | 90 min | 0 min | 30 min | 60 min | 90 min |
| 1 | 80 | 46 | 31 | | 95 | 59 | 55 | 52 |
| 2 | 26 | 27 | 29 | 25 | 88 | 41 | 13 | |
| 3 | | | | | 93 | 43 | 26 | 24 |
| 4 | | | | | 91 | 50 | 42 | 41 |
| 5 | | | | | 95 | 60 | 60 | 60 |
| 6 | 50 | 40 | 35 | 30 | 82 | 63 | 60 | 55 |
| 22 | | | | | 64 | 22 | 24 | |
| 23 | | | | | 52 | 22 | 21 | 22 |
| 24 | 36 | 11 | 0 | 9 | 58 | 5 | 18 | 27 |

TABLE 5

LH-RH inhibiting activities of Ac—D—Nal(2)—D—Phe(4Cl)—D—Pal(3)—Ser—Arg—D—Lys[$A_2$pr(Y)$_2$]—Leu—Arg—Pro—D—Ala—NH$_2$ antagonists in perfused rat pituitary cell system at various molar ratios of antagonist to LH-RH

| | % inhibition of LH response at different antagonist to LH-RH ratio | | | | | | | |
|---|---|---|---|---|---|---|---|---|
| | 1:1 | | | | 3:1 | | | |
| No. of Peptide | 0 min | 30 min | 60 min | 90 min | 0 min | 30 min | 60 min | 90 min |
| 7 | 57 | 51 | 45 | 41 | 96 | 78 | 70 | 58 |
| 8 | 64 | 39 | 27 | 22 | 99 | 66 | 47 | 37 |
| 9 | | | | | 90 | 72 | | |
| 14 | | | | | 80 | 63 | 51 | 53 |
| 15 | 44 | 41 | 22 | 23 | 99 | 60 | 34 | 21 |
| 16 | 52 | 33 | 24 | 28 | | | | |
| 18 | | | | | 90 | 71 | 58 | 54 |
| 19 | 20 | 20 | 0 | 0 | | | | |
| 25 | 57 | 49 | 43 | | 85 | 69 | 62 | 57 |
| 26 | 70 | 52 | 37 | | 90 | 75 | 62 | 57 |

TABLE 6

Effect of 25 μg/day dose of Peptide 8 on the growth of Dunning R3327 prostate cancer in rats.

| Time (week) | Size of tumor (mm$^3$) Control group | Size of tumor (mm$^3$) Treated group |
|---|---|---|
| 0 | 4326 ± 1891* | 4001 ± 1617 |
| 1 | 6901 ± 2968 | 5459 ± 1863 |
| 2 | 9174 ± 4507 | 5892 ± 1938 |
| 3 | 9465 ± 4349 | 6357 ± 2327 |
| 4 | 12582 ± 6659 | 6237 ± 2974** |
| 5 | 12230 ± 4848 | 7447 ± 3481** |
| 6 | 14732 ± 6597 | 8038 ± 4374** |
| 7 | 17796 ± 8602 | 8129 ± 3525*** |

*SD
**p <0.05
***p <0.01

We claim:
1. A compound of the formula

X—$R^1$—$R^2$—$R^3$-Ser-$R^5$—$R^6$(A$Y_2$)-Leu-Arg-Pro-D-Ala-NH$_2$ and the pharmaceutically acceptable salts thereof, wherein
$R^1$ is D-Phe, D-Phe(4Cl), D-Nal(1) or D-Nal(2),
$R^2$ is D-Phe or D-Phe(4Hl),
$R^3$ is D-Trp or D-Pal(3),
$R^5$ is Tyr or Arg, $R^6$ is D-Lys or D-Orn,
Hl is fluoro, chloro or bromo
X is a lower alkanoyl group of 2-5 carbon atoms,
A is a diaminoacyl residue having the formula

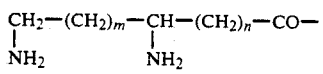     II where
m is 0 or 1,
n is 0 or 1,
Y is $Y^1$ or $Y^2$, wherein
   $Y^1$ is an acyl group derived from straight or branched chain aliphatic or alicyclic carboxylic acids having from 3 to 12 carbon atoms or aromatic carboxylic acids of 6 or 10 ring carbon atoms,
   $Y^2$ is carbamoyl or a $C_1$-$C_3$ alkyl-substituted carbamoyl group having the formula

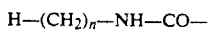     III where n is 0-3.

2. A peptide of claim 1, wherein Y is $Y^1$, where $Y^1$ is formyl, acetyl, propionyl, butyryl, i-butyryl, cyclohexanoyl or benzoyl.

3. A peptide of claim 2, wherein $R^1$ is D-Nal(2), $R^2$ is D-Phe(4Cl), $R^3$ is D-Pal(3), $R^5$ is Tyr, $R^6$ is D-Lys, X is acetyl and A is 2,3-diaminopropionyl.

4. A peptide of claim 3, wherein $Y^1$ is formyl.
5. A peptide of claim 3, wherein $Y^1$ is acetyl.
6. A peptide of claim 3, wherein $Y^1$ is propionyl.
7. A peptide of claim 2, wherein $R^1$ is D-Nal(2), $R^2$ is D-Phe(4Cl), $R^3$ is D-Pal(3), $R^5$ Tyr, $R^6$ is D-Lys, X is acetyl and A is 2,4-diaminobutyryl.
8. A peptide of claim 7, wherein $Y^1$ is formyl.
9. A peptide of claim 7, wherein $Y^1$ is acetyl.
10. A peptide of claim 7, wherein $Y^1$ is propionyl.
11. A peptide of claim 2, wherein $R^1$ is D-Nal(2), $R^2$ is D-Phe(4Cl), $R^3$ is D-Pal(3), $R^5$ is Arg, $R^6$ is D-Lys, X is acetyl and A is 2,3-diaminopropionyl.
12. A peptide of claim 11, wherein $Y^1$ is formyl.
13. A peptide of claim 11, wherein $Y^1$ is acetyl.
14. A peptide of claim 11, wherein $Y^1$ is propionyl.
15. A peptide of claim 2, wherein $R^1$ is D-Nal(2), $R^2$ is D-Phe(4Cl), $R^3$ is D-Trp, $R^5$ is Arg, $R^6$ is D-Lys, X is acetyl and A is 2,3-diaminopropionyl.
16. A peptide of claim 15, wherein $Y^1$ is formyl.
17. A peptide of claim 15, wherein $Y^1$ is acetyl.
18. A peptide of claim 1, wherein Y is $Y^2$, where $Y^2$ is carbamoyl, N-methyl-carbamoyl or N-ethyl-carbamoyl.
19. A peptide of claim 18, wherein $R^1$ is D-Nal(2), $R^2$ is D-Phe(4Cl), $R^3$ is D-Pal(3), $R^5$ is Tyr, or Arg $R^6$ is D-Lys, X is acetyl and A is 2,3-diaminopropionyl or 2,4-diaminobutyryl.
20. A peptide of claim 19, wherein $Y^2$ is carbamoyl.
21. A peptide of claim 19, wherein $Y^2$ is ethylcarbamoyl.

* * * * *

UNITED STATES PATENT AND TRADEMARK OFFICE
CERTIFICATE OF CORRECTION

PATENT NO. : 5,171,835
DATED : December 15, 1992
INVENTOR(S) : Janaky, et al

It is certified that error appears in the above-indentified patent and that said Letters Patent is hereby corrected as shown below:

Column 2, line 18, delete "duced", insert --duce--.
  line 37, before citrulline and homocitrulline, insert --D- --, both instances.
  line 49, delete "accepted for publication", insert --88, 884-848, 1991--.

Column 3, line 15, delete "endematogenic", insert --edematogenic--.
  line 56, delete "methybenzylhydrylamine", insert --methylbenzhydrylamine--.

Column 5, line 39, delete "isometric", insert --isomeric--.

Column 8, line 44, delete "accepted for publication", insert --87, 7100-7104, 1990--.
  line 67, delete "accepted for publication", insert --88, 844-848, 1991--.

Column 11, line 21, delete "$X^6$", insert --$X^8$--.
  line 50, delete "imidazyl", insert --imidazole--.

Column 12, lines 41 and 57, before "$A_2$pr", delete "DL-", each instance.

Column 15, line 24, delete "18 h", insert --18 min--.

UNITED STATES PATENT AND TRADEMARK OFFICE
CERTIFICATE OF CORRECTION

PATENT NO. : 5,171,835
DATED : December 15, 1992
INVENTOR(S) : Janaky, et al

It is certified that error appears in the above-indentified patent and that said Letters Patent is hereby corrected as shown below:

Column 16, line 37, delete "Ser-Arg", insert --Ser-Tyr--.
line 39, after "(Bz)$_2$", insert --}--.
line 40, delete "VIb and", insert --VIa and VIb with--.
line 42, delete "with carbodiimide", insert --by carbodiimide method--.
line 45, delete "VIb", insert --VIa--.
line 47, after "18 hours.", insert --A similar reaction was performed with Preparation VIb--.
line 57, delete "Via", insert --VIa--.
line 58, delete "diminopriopionic", insert --diaminopriopionic--.
lines 67-68, delete "respectively".

Column 17, line 12, delete "carbamylating", insert --carbamoylating--.

Column 18, line 17, delete "Tyr-D-Tyr-D-Lys[A$_3$pr", insert --Tyr-D-Lys[A$_2$pr--.

Signed and Sealed this

First Day of March, 1994

BRUCE LEHMAN

Attest:

Attesting Officer

Commissioner of Patents and Trademarks